United States Patent [19]
Cohen et al.

[11] Patent Number: 5,869,058
[45] Date of Patent: Feb. 9, 1999

[54] PEPTIDES USED AS CARRIERS IN IMMUNOGENIC CONSTRUCTS SUITABLE FOR DEVELOPMENT OF SYNTHETIC VACCINES

[75] Inventors: Irun R. Cohen; Matityahu Fridkin, both of Rehovot, Israel; Stephanie Konen-Waisman, Köln, Germany

[73] Assignee: Yeda Research and Development Co. Ltd., Israel

[21] Appl. No.: 774,325

[22] PCT Filed: Mar. 7, 1996

[86] PCT No.: PCT/US95/06575

§ 371 Date: May 25, 1994

§ 102(e) Date: May 24, 1995

[87] PCT Pub. No.: WO95/31994

PCT Pub. Date: Nov. 30, 1995

[30] Foreign Application Priority Data

May 25, 1994 [IL] Israel ......................................... 109790

[51] Int. Cl.$^6$ ...................... A61K 39/385; A61K 39/112; A61K 39/09
[52] U.S. Cl. .................................. 424/194.11; 424/197.1; 424/257.1; 424/184.1; 424/185.1; 424/190.1; 424/194.1; 424/282.1; 530/326; 530/348; 530/350; 530/402; 530/403; 514/12
[58] Field of Search .............................. 424/197.1, 282.1, 424/194.11, 257.1, 184.1, 185.1, 190.1, 194.1; 514/12; 530/326, 348, 350, 403, 402

[56] References Cited

U.S. PATENT DOCUMENTS

| | | |
|---|---|---|
| 4,689,397 | 8/1987 | Shinnick et al. . |
| 4,818,527 | 4/1989 | Thornton et al. . |
| 5,114,844 | 5/1992 | Cohen et al. . |
| 5,154,923 | 10/1992 | Van Eden et al. . |
| 5,196,512 | 3/1993 | Bianchi et al. . |

FOREIGN PATENT DOCUMENTS

| | | |
|---|---|---|
| 0378881 | 7/1990 | European Pat. Off. . |
| 0 419 569 B1 | 4/1991 | European Pat. Off. . |
| WO 92/08488 | 5/1992 | WIPO . |
| WO 93/17712 | 9/1993 | WIPO . |

OTHER PUBLICATIONS

Adam, A. *Synthetic Vaccines* Wiley & Sons, Inc. New York 1985 pp. 123–124.
Warren et al. Ann. Rev. Immunol. 4:369 1986.
Lussow et al. Eur. S. Immunol 21: 2297–2302, 1991.
Barrios et al. Eur. S. of Immunol. 22:1365, 1992.
A.R. Lussow et al., Immunology Letters, 25:225–264 (1990).
D. Young et al., Proc. Natl. Acad. Sci. USA 85:4267–4270 (1988).
Demotz, S., et al., "A Novel and Simple Procedure for Determining T Cell Epitopes in Protein Antigens," Journal of Immunological Methods, Issued 1989, 122:67–72 (abstract on page 67).
Elias, D., et al., "Vaccination Against Autoimmune Mouse Diabetes With a T–Cell Epitope of the Human 65–kDa Heat Shock Protein," Proc. Natl. Acad. Sci. USA, issued Apr. 1991, 88:3088–3091 (abstract on page 3088).
Van der Zee, R., "Efficient Mapping and Characterization of a T–Cell Epitope By the Simultaneous Synthesis of Multiple Peptides," Eur. J. Immunol., issued 1989, 19:43–47 (abstract on page 43).
Avery, O.T. and Goebel, W.F., "Chemo–immunological Studies on Conjugated Carbohydrate–Proteins," J. Exp. Med. 50:533–550 (1929).
Barrios, C. et al., "Mycobacterial Heat–shock Proteins as Carrier Molecules. II: The Use of the 70–kDa Mycobacterial Heat–shock Protein as Carrier for Conjugated Vaccines Can Circumvent the Need for Adjuvants and Bacillus Calmette Guérin Priming," Eur. J. Immunol. 22:1365–1372 (1992).
Brett, S.J. et al., "Differential Pattern of T Cell Recognition of the 65–kDa Mycobacterial Antigen Following Immunization with the Whole Protein or Peptides," Eur. J. Immunol. 19:1303–1310 (1989).
Cohen, I.R. and Young, D.B., "Autoimmunity, Microbial Immunity and the Immunological Homunculus," Immunology Today 12:105–110 (1991).
Cox et al., "Orientation of Epitopes influences the Immunogenicity of Synthetic Peptide Dimers," Eur. J. Immunol. 18:2015–2019 (1988),
Elias, D. et al., "Induction and Therapy of Autoimmune Diabetes in the Non–obese Diabetic (NOD/Lt) Mouse by a 65–kDa Heat Shock Protein," Proc. Natl. Acad. Sci. USA 87:1576–1580 (1990).
Lamb, J.R. et al., "Mapping of T Cell Epitopes Using Recombinant Antigens and Synthetic Peptides," EMBO Journal 6:1245–1249 (1987).
Lussow, A.R. et al., "Towards Vaccine Optimisation," Immunol. Letters 25:255–264(1990).
Lussow, A.R. et al., "Mycobacterial Heat–shock Proteins as Carrier Molecules," Eur. J. Immunol. 21:2297–2302 (1991).
Merrifield, R.B., "Solid Phase Peptide Synthesis. I. The Synthesis of a Tetrapeptide," J. Am. Chem. Soc. 85:2149–2154 (1963).

(List continued on next page.)

*Primary Examiner*—Thomas M. Cunningham
*Assistant Examiner*—Martha Lubet
*Attorney, Agent, or Firm*—Pennie & Edmonds LLP

[57] ABSTRACT

The invention relates to conjugates of poorly immunogenic antigens, e.g., peptides, proteins and polysaccharides, with a synthetic peptide carrier constituting a T cell epitope derived from the sequence of *E. coli* hsp65 (GroEL), or an analog thereof, said peptide or analog being capable of increasing substantially the immunogenicity of the poorly immunogenic antigen. A suitable peptide according to the invention is Pep278e, which corresponds to positions 437–453 of the *E. coli* hsp65 molecule.

19 Claims, 5 Drawing Sheets

OTHER PUBLICATIONS

Munk, M.E. et al., "T Cell Responses of Normal Individuals Towards Recombinant Protein Antigens of *Mycobacterium Tuberculosis* ," Eur. J. Immunol. 18:1835–1838 (1988).

Munk, M.E. et al., "T Lymphocytes from Healthy Individuals with Specificity to Self–epitipes Shares by the Mycobacterial and Human 65–Kilodalton Heat Shock Protein," J. Immunol. 143:2844–2849 (1989).

Pearson, C.M., "Experimental Models in Rheumatoid Disease," Arthritis and Rheumatism 7:80–86 (1964).

Szu, S.C. et al., "Comparative Immunogenicities of Vi Polysaccharide–Protein Conjugates Composed of Cholera Toxin or Its B Subunit as a Carrier Bound to High–or Lower–Molecular–Weight Vi," Infection and Immunity 57:3823–3827 (1989), Verbon, A. et al., "Murine and Human B Cell Epitope Mapping of the *Mycobacterium Tuberculosis* 10–kD Heat Shock Protein Using Overlapping Peptides," Clin. Exp. Immun. 86:6–11 (1991), Young, D. et al., "Stress Proteins are Immune Targets in Leprosy and Tuberculosis," Proc. Natl. Acad. Sci. USA 85:4267–4270 (1988).

Barrios, C., et al., 1992, Mycobacterial heat–shock proteins as carrier molecules. II: The use of the 70–kDa mycobacterial heat–shock protein as carrier for conjugated vaccines can circumvent the need for adjuvants and Bacillus Calmette Guerin priming, *Chemical Abstracts* 117:632.

Bianco, A.E., et al. , 1986, A repetitive antigen of *Plasmodium falciparum* that is homologous to heat shock protein 70 of *Drosophila melanogaster* , Proc. Natl. Acad. Sci. USA 83:8713–8717.

Dostal, V.V., et al., 1977, Die Herpes–simplex–Virus–(HSV–1)–und HSV–2)Infektion, ihre klinische und onkogene Bedeutung, *Wiener klinische Wochenschrift* 89(11):741–748.

Edgington, S.M., 1995, Therapeutic Applications of Heat Shock Proteins, Bio/technology 13:1442–1444.

Hansen, K., et al., 1988, Immunochemical Charaterization of and Isolation of the Gene for a *Borrelia burgdorferi* Immunodominant 60–Kilodalton Antigen Common to a Wide Range of Bacteria, *Infection and Immunity* 56(8):2047–2053.

Hedstrom, R., et al., 1987, A Major Immunogen In Schistosoma Mansoni infections Is Homologous To The Heat––Shock Protein Hsp70, *Jounal of Experimental Medicine* 165:1430–1435.

Hindersson, P., et al., 1987, Cloning and Expression of *Treponema pallidum* Common Antigen (Tp–4) in *Escherichia coli* K12, *Journal of General Microbiology* 133:587–596.

Husson, R.N., et al., 1987, Genes for the major protein antigens of *Mycobacterium tuberculosis:* The etiologic agents of tuberculosis and leprosy share an immunodominant antigen, Proc. Natl. Acad. Sci. USA 84:1679–1683.

Lamb, J.R., et al., 1989, Stress proteins may provide a link between the immune response to infection and autoimmunity, *International Immunology* 1(2):190–196.

Shinnick, T.M., et al., 1988, The *Mycobacterium tuberculosis* 65–Kilodalton Antigen Is a Heat Shock Protein Which Corresponds to Common Antigen and to the *Escherichia coli* GroEL Protein, *Infection and Immunity* 56(2):446–461.

Thole, J.E.R., et al., 1987, Characterization, Sequence Determination, and Immunogenicity of a 64–Kilodalton Protein of *Mycobacterium bovis* BCG Expressed in *Escherichia coli* K–12, *infection and Immunity* 55(6):1466–1475.

Thole, J.E.R., et al., 1988, Antigenic relatedness of a strongly immunogenic 65 kDA mycobacterial protein antigen with a similarly sized ubiquitous bacterial common antigen, *Microbial Pathogenesis* 4:71–83.

Verloes, R., et al., 1981, Successful Immunotherapy With Micrococcus, BCG Or Related Polysaccharides On L1210 Leukaemia After BCNU Chemotherapy, Br. J. Cancer 43:201–209.

Vodkin, M.H., et al., 1988, A Heat Shock Operon in *Coxiella burnetii* Produces a Major Antigen Homologous to a Protein in Both Mycobacteria and *Escherichia coli* , *Journal of Bacteriology* 170(3):1227–1234.

Whittle, H.C., et al., 1987, Trials of intradermal hepatitis B vaccines in Gambian children, *Annals of Tropical Paediatrics* 7:6–9.

Yashphe, D.J., et al., 1969, Modulation of the immune response by a methanol extraction residue of BCG, Isr. J. Med. Sci. 5(3):440.

Young, D.B., 1988, Stress–Related Proteins Are Major Antigens In Leprosy And Tuberculosis, UCLA *Keystone Symposium* Abstract No. P432, p. 297.

Young, D., et al. 1989, Stress–Induced Proteins As Antigens In Infectious Diseases, *Stress–Induced Proteins* , p. 275–285.

Zerial, A., et al., 1981, Effect of Immunostimulating Agents on Viral Infections, Acta microbiol. Acad. Sci. hung. 28:325–337.

Zykov, M.P., et al., 1981, Influenza Vaccine Response Following its Simultaneous Application with BCG, Crkrank. Atm.–Org. 156:203–211.

Zykov, M.P., et al., 1985, Modulation Of Humoral Immune Response To Influenze Vaccines By BCG, Acta. virol. 29:403–409.

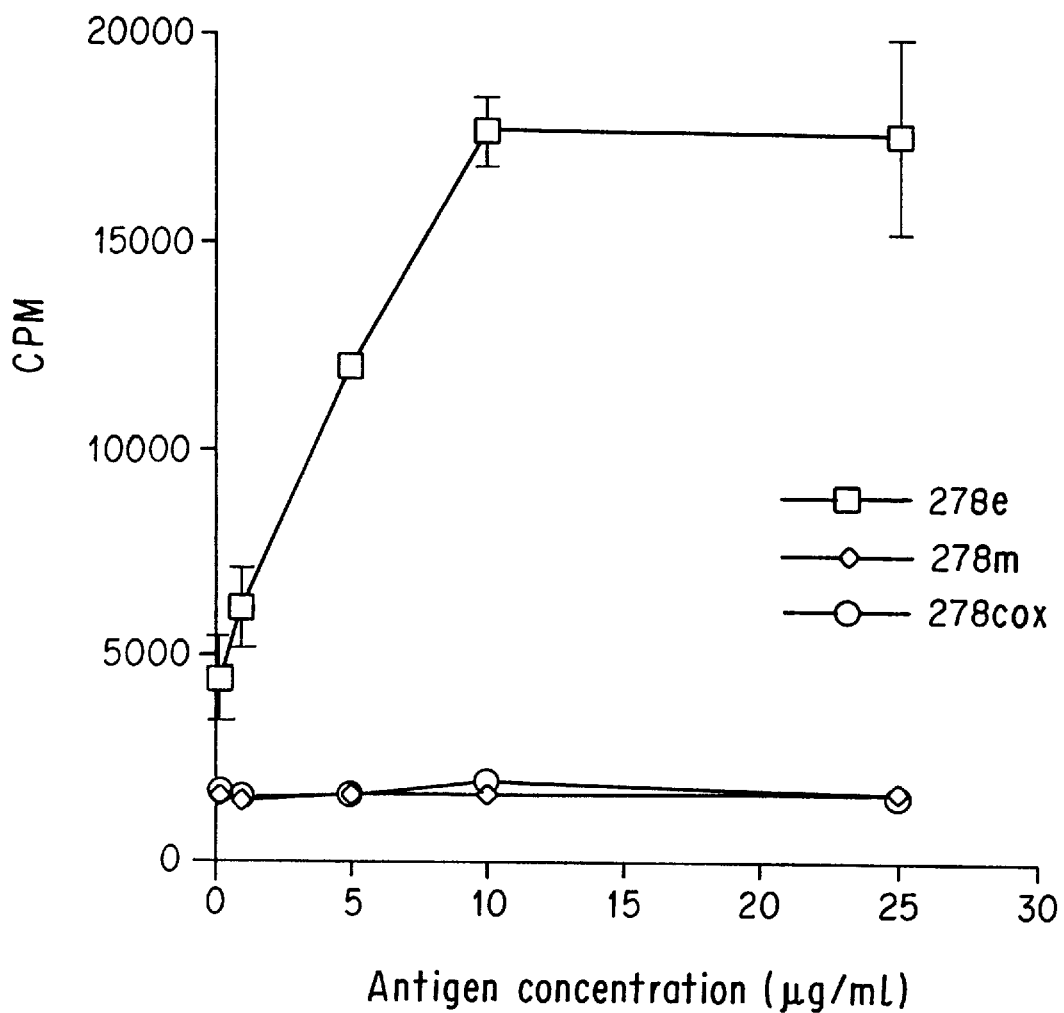
F I G. 1

PEPTIDES USED AS CARRIERS IN IMMUNOGENIC CONSTRUCTS SUITABLE FOR DEVELOPMENT OF SYNTHETIC VACCINES

This is a continuation of Application No. PCT/US95/06575 filed May 24, 1995, which claims priority benefits of Israel Application No. 109790 filed May 25, 1994.

FIELD OF THE INVENTION

A synthetic peptide, is described having an amino acid sequence corresponding to that of a T cell epitope of the heat shock protein 65 of *E. coli* (hereinafter GroEL) and its analogs able to be recognized in association with a range of mouse major histocompatibility complex (MHC) molecules. Said peptide or its analogs can be used as synthetic carriers in the preparation of immunogenic conjugates consisting of said peptides and a natural or synthetic hapten derived from a pathogenic agent of interest.

BACKGROUND OF THE INVENTION

Immunization against infection caused by pathogenic microorganism (bacteria, viruses and parasites) is generally achieved by inoculating an individual with the natural antigen (attenuated or killed microorganism) or parts of said infectious agent (for example detoxified microbial products) in order to stimulate a protective immune response able to neutralize the pathogenic microbe or its deleterious effects.

Limited availability of the natural antigenic substance, risks involved in handling pathogenic material as well as storage problems stimulated the interest in the development of subunit vaccines. Isolated protective epitopes nevertheless are often characterized by their poor immunogenicity. The carbohydrate capsules of bacteria are an example of such coats: They are not easily recognized by T cells and therefore the immune response to these antigens is deprived of T cell help, T cell memory, IgG class switch, and affinity maturation. Such an immune response is inefficient and resistance to infection with bacteria encoated with carbohydrate capsules is not easily obtained by vaccination, with bacterial carbohydrates. Peptide epitopes too may be poorly immunogenic, the absence of a T cell epitope and the genetically restricted immune response being the reason.

It is now well established that most antigens require T cell help to induce B cells to produce antibodies. Conjugating a "helper" or T cell determinant to a B cell-specific antigen was shown to induce humoral immune responses to the coupled B cell epitope. The discovery by Avery & Goebel (1929) that coupling of polysaccharides to protein carriers increases immunogenicity has recently been used for the preparation of vaccines for human use. Both in humans and in rodents these conjugates behave like T cell dependent antigens by exhibition of immunological memory. There are similarities between conjugate polysaccharide vaccines and protein carrier-hapten systems. Thus the capsular polysaccharide (CPS) conjugates are able to induce protective levels of CPS antibodies in infants, while CPS alone is not. It is possible that the superior immunogenicity of conjugates compared to that of pure polysaccharides is due to the help by carrier-specific T cells, as has been demonstrated in the carrier-hapten system in rodents.

In most cases, T cell independent (T-ind) antigens have been coupled to large immunogenic carrier proteins such as tetanus toxoid, cholera toxin or diphtheria toxoid. Nevertheless, besides dosage limitations and the risk of sensitization to the carrier itself, as reported for tetanus toxoid, the immunological response to high molecular weight carrier molecules harboring stimulatory as well as suppressive T cell epitopes is not very predictable. It has been shown that the antibody response to a hapten coupled to a carrier protein can also be inhibited when the recipient has been previously immunized with the unmodified protein. This phenomenon has been termed carrier-induced epitope suppression and was recently demonstrated to occur with a number of hapten-protein conjugates (Herzenberg & Tokuhisa, 1982). Since the development of more potent conjugate vaccines against a large number of extremely infectious organisms is still important, efforts are being made to search for more appropriate carrier molecules providing the needed T cell epitopes. Universally immunogenic T cell epitopes, defined by specific peptides with sharply outlined immunological characteristics, might represent a new generation of such alternative molecules. T cell epitopes of various sorts have been used for this purpose before. However, to trigger a strong memory response when the host meets the infectious agent after vaccination, the T cell carrier epitope should be present along with the specific B cell epitope. This fact would seem to require that a different T cell carrier be used for each infectious agent. Highly abundant proteins well recognized by the immune system might be an appropriate source for peptides serving this purpose.

Studies using a wide variety of proteins, both those closely related to self and those phylogenetically distantly related, have shown that the majority of T cells are focused onto a few immunodominant epitopes with a minority responding to other, subdominant determinants. This hierarchy of determinant utilization by T cells could result from a combination of factors including differential affinities for the available MHC molecules, the diversity of the T cell repertoire, internal competition for MHC-binding sites and fine differences in processing (Babitt et al, 1985; Kappler et al, 1987; Brett et al, 1988)

Evidence is accumulating that proteins belonging to the family of heat shock proteins (hsp's) are major antigens of many pathogens (Young et al, 1988). Hsp's were first described and later named due to their production by cells exposed to sudden elevations in temperature. The hsp's include proteins of various molecular weights,. including 20 kD, 60 kD, 65–68 kD, 70 kD, 90 kD, 110 kD, and others. It is now apparent that hsp's are induced in all cells by many different environmental insults, including oxidative injury, nutrient depletion and infection with intracellular pathogens; the hsp response enables the cell to survive under otherwise unfavorable conditions. Although cellular stress increases the synthesis of hsp's, many hsp's are also constitutively expressed and play an essential role in normal cell function. The hsp response is ubiquitous throughout the pro- and eukaryotic kingdoms and hsp's belong to some of the most conserved molecules.

Hsp65, as a representative member of the proteins belonging to the hsp family, can be considered to be a dominant antigen because infection or immunization with many different bacteria induces antibodies and T cells specific for the hsp65 molecule (Young et al, 1988). In mice immunized with Mycobacterium tuberculosis, 20% of all T cells which respond to the bacterium, are specific for hsp65. Interestingly, T cells with reactivity to hsp65 have also been identified in normal healthy individuals lacking any clinical signs of disease (Munk et al, 1988).

Lussow et al. (1990) showed that priming of mice with live Mycobacterium tuberculosis var.bovis (BCG) and immunization with the repetitive malaria synthetic peptide (NANP)$_{40}$, conjugated to purified protein derivative (PPD), led to the induction of high and long-lasting titers of anti-peptide IgG antibodies. Later on, Lussow et al. (1991) reported that the mycobacterial hsp65 as well as the hsp65 of E. coli (GroEL) acted as carrier molecules in mice, previously primed with BCG, for the induction of high and long-lasting titers of IgG against the repetitive malaria synthetic peptide (NANP)$_{40}$. Anti-peptide antibodies were induced when the malaria peptide, conjugated to the mycobacterial or E. coli hsp, was given in the absence of any adjuvants.

Barrios et al. (1992) have shown that mice immunized with peptides or oligosaccharides conjugated to the 70 kD hsp produced high titers of IgG antibodies in the absence of any previous priming with BCG. The anti-peptide antibody response persisted for at least 1 year. This adjuvant-free carrier effect of the 70 kD hsp was T cell dependent, since no anti-peptide nor anti70 kD IgG antibodies were induced in athymic nu/nu mice. Previous immunization of mice with the 65 kD or 70 kD hsp did not have any negative effect on the induction of anti-peptide IgG antibodies after immunization with hsp-peptide conjugates in the absence of adjuvants. Furthermore, preimmunization with the 65 kD hsp could substitute for BCG in providing an effective priming for the induction of anti-(NANP)$_{40}$ antibodies. The carrier effect of mycobacterial hsp65 and hsp70 for conjugated peptides was demonstrated also in non-human primates (Perraut et al, 1993).

It can be assumed that some T cell epitopes within the sequence of the bacterial hsp65 protein show immunodominance and are able to induce immunological memory, whereas others do not express privileged immunological recognition or are involved in the induction of autoimmune diseases. Distinguishing between functionally different T cell epitopes, binding to several different MHC molecules, may lead to the identification of universally immunogenic peptides, which can qualify as safe, defined, and potent alternatives for carrier molecules of T-ind antigens.

Israel Patent Application No. 102687 of the same applicants describes specific T cell epitopes of human hsp65, and analogs thereof, conjugated to poorly immunogenic molecules.

None of the above mentioned references describes specific T cell epitopes derived from the sequence of hsp65 of E. coli (GroEL) conjugated to poorly immunogenic molecules.

SUMMARY OF THE INVENTION

It is an object of the present invention to provide a method for enhancing the immunogenicity of poorly immunogenic antigen molecules, thus converting them to suitable antigens for immunization.

For this purpose, the present invention provides conjugates of a poorly immunogenic antigen and a synthetic peptide carrier constituting a T cell epitope derived from the sequence of E. coli hsp65 (GroEL) or an analog thereof, said peptide or analog being capable of increasing substantially the immunogenicity of the poorly immunogenic antigen.

Any peptide, or analog thereof, derived from GroEL constituting a T cell epitope and able to increase substantially the immunogenicity cm the poorly immunogenic antigen, can be used in the invention.

A preferred peptide according to the invention, herein designated 278e, corresponds to positions 437–453 of the GroEL molecule, and has the sequence:

437                           453
N E D Q N V G I K V A L R A M E A (SEQ ID NO: 1)

The poorly immunogenic antigen molecule may be a peptide, a polypeptide or a protein, e.g., a peptide derived from HIV virus or from malaria antigen, or a bacterial polysaccharide, e.g., capsular polysaccharides from Haemophilus influenzas type b, Streptococcus pneumoniae, Neisseria meningitidis, group B Streptococci, E. coli type Kl, Salmonella, such as Salmonella typhi, etc.

The carrier peptide is covalently linked to the poorly immunogenic antigen molecule, either directly or through a spacer.

The invention further relates to vaccines comprising a conjugate of the invention or a mixture of the poorly immunogenic antigen and the suitable peptide carrier.

In another embodiment, the invention relates to a method of immunization of a mammalian host which comprises administering to said host an effective amount of a conjugate of the invention, or co-administering effective amounts of a poorly immunogenic antigen molecule and of a synthetic peptide carrier constituting a T cell epitope derived from the sequence of GroEL, or an analog thereof, said peptide or analog being able to enhance substantially the immunogenicity of the poorly immunogenic antigen.

BRIEF DESCRIPTION OF THE DRAWINGS

FIG. 1 shows lymph node proliferation to 278 epitopes 278e, 278m and 278cox after immunizing BALB/C mice with 20 µg 278 epitope emulsified in incomplete Freund's adjuvant (IFA).

DETAILED DESCRIPTION OF THE INVENTION

Figure 2:
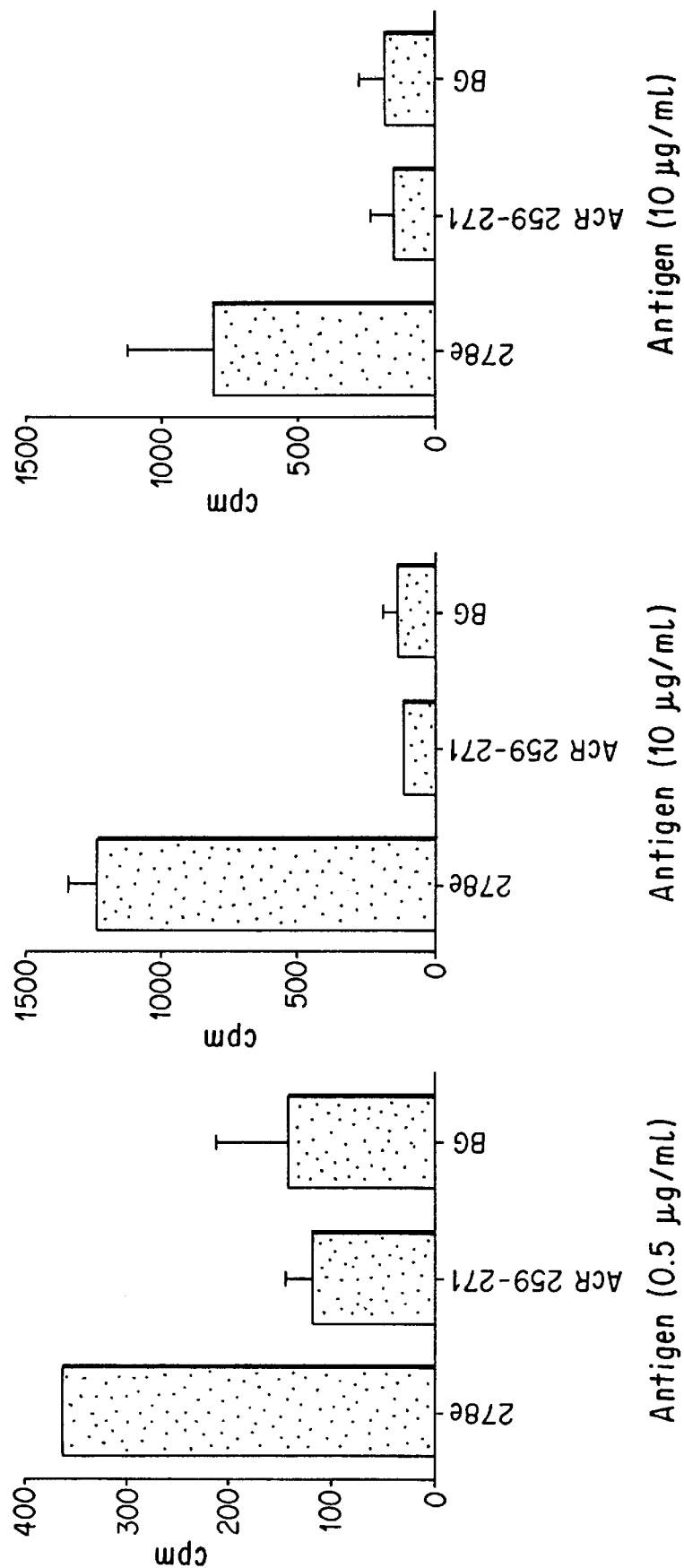
FIGS. 2a–c show lymph node proliferation to 278e and to control peptide ACR 259–271 after immunizing B10RIII mice (2a), B10.BR mice (2b), and B10.S mice (2c) with 20 µg 278e emulsified in IFA.

Preferred conjugates according to the invention are formed by covalently linking peptide 278e with a bacterial polysaccharide, e.g., the capsular polysaccharide (CPS) Vi of Salmonella typhi, hereinafter referred to as Vi or Vi-fragments, a linear homopolymer of poly-α-(1–4) GalNAc variably O-acetylated at the $C_3$-position, as shown in scheme 1. The native Vi molecule has a molecular weight of about 3×10$^3$ kD (Vi). Vi-fragments (about 45 kD) are prepared by ultrasonic cleavage, which does not alter the structure of its monomeric units and which produces a relatively homogeneous polysaccharide (Stone & Szu, 1988). Vi/Vi-fragments alone, like other CPSs, do not elicit a booster response in mammals, either in animals or in humans, when reinjected, but its immunogenicity is increased when presented as a conjugate according to the invention coupled to a suitable peptide derived from GroEL or an analog thereof, or in a mixture with such a peptide or analog. Reinjection of the Vi-peptide conjugate induces an increase in the level of anti-Vi antibodies (booster effect), which are mainly represented by the IgG isotype.

Peptide 278e of the present invention is clearly distinct from peptides 278h and 278m of above-mentioned Patent Application No. 102687.
278e N E D Q N V G I K V A L R A M E A (SEQ ID NO:1)
278h N E D Q K I G I E I I K R T L K I (SEQ ID NO:2)
278m N E D Q K I G I E I I K R A L K I (SEQ ID NO:3)

Peptide 278e is a highly charged and hydrophobic molecule. Thus, 5 out of 17 constituent amino acids are ionized (3 negatively and 2 positively) at physiological pH. Five amino acid residues are hydrophobic. In addition, 3 residues are amidated and capable of establishing substantial hydrogen bonding. The peptide is further characterized as possessing a polar negatively-charged N-terminal domain, a polar charged C-terminal domain and a highly hydrophobic core. 278e can be modified while retaining activity. In order to preserve activity, however, its overall structural features should be maintained. Thus, positions 2, 3 and 16 can be either occupied by either E or D, and positions 9 and 13 by either K or R. Conservation of the charge at positions 9 and 13 (positive to negative and vice-versa) will lead to active peptides. A hydrogen bond forming amino acid, preferably N and Q, should occupy positions 1 and 4.

Hydrophobicity at positions 6, 8, 10, 12 and 15 should be maintained by incorporating hydrophobic amino acids, natural, e.g., I, L, V, M or F, or unnatural, e.g., norleucine (Nle) or norvaline (Nva).

The term "analogs" in the present invention relates to peptides obtained by replacement, deletion or addition of amino acid residues to the sequence of the T cell epitope, as long as they have the capability of enhancing substantially the immunogenicity of poorly immunogenic antigen molecules. Analogs, in the case of peptide 278e, are peptides such that at least 70%, preferably 90–100%, of the electric properties and of the hydrophobicity of the peptide molecule are conserved. These peptides can be obtained according to the instructions in the paragraph herein before.

The peptides according to the invention may have all the optically active amino acid residues in L or D form, or some of the amino acid residues are in L and others are in D form.

By "substantially increasing the immunogenicity of a poorly immunogenic antigen molecule" it is meant to comprise both the induction of an increase in the level of antibodies against said antigen as well as the presentation of said antibodies as mainly of the IgG isotype.

The peptide carrier may be linked to the antigen molecule directly or through a spacer.

A direct link between the peptide and Vi or Vi-fragments is shown in Scheme 1 herein, where the conjugate

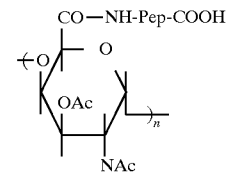

is obtained by Procedure 1 as described hereafter.

The spacer may have the formula —O—R—CO or —NH—R—CO, thus forming an ester or amide, respectively, with the carboxyl group of Vi or Vi-fragments and a peptide bond with the terminal amino group of the peptide; or —NH—R—CH$_2$—, wherein R is a saturated or unsaturated hydrocarbon chain optionally substituted and/or interrupted by one or more aromatic radicals or by heteroatoms such as O, S or N. Preferably, R is an aliphatic hydrocarbon chain containing 3–16 carbon atoms, such as the residue of ε-aminocaproic acid.

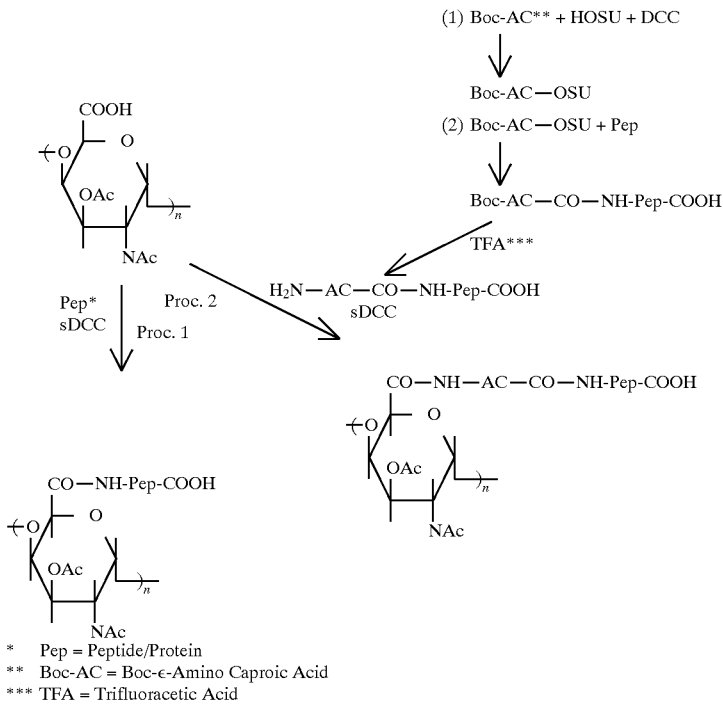

Scheme 1

\*   Pep = Peptide/Protein
\*\*  Boc-AC = Boc-ε-Amino Caproic Acid
\*\*\* TFA = Trifluoracetic Acid The conjugate of the formula:

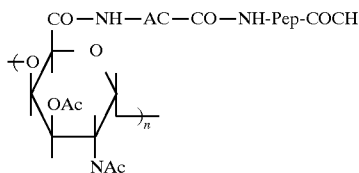

CO—NH—AC—CO—NH-Pep-COCH in which Ac is acetyl, AC is the residue of ε-aminocaproic acid, Pep is the residue of the peptide carrier 278e or an analog thereof and the saccharide residue represents a repeating unit of the Vi capsular polysaccharide (Vi or vi-fragments) of Salmonella typhi, may be prepared by Procedure 2 depicted in Scheme 1 and described in detail hereafter.

The conjugates wherein the spacer is —NH—R—$CH_2$— are obtained by reduction of —NH—R—CO— groups or by alkylation cm the peptidic amino terminus with —NH—R—$CH_2$—X, when X is an appropriate leaving group such as an halide.

The invention further relates to vaccines comprising a conjugate of the invention. These vaccines may be administered by any suitable route, e.g., orally or via the subcutaneous route in suitable vehicles for human and veterinary purposes.

The invention will now be illustrated by the following non-limiting examples:

EXAMPLES

In the examples, the following materials and methods will be used.

Materials & Methods a. Materials: All solvents and chemicals were of analytical grade and obtained from Aldrich, U.S.A., unless otherwise mentioned.

b. Peptide synthesis: Peptide 278e was prepared with an automated synthesizer (Applied Biosystem model 430A, Germany) using the company's protocols for t-butyloxycarbonyl (BOC) strategy (Kent et al, 1984).

The following control peptides were synthesized: Peptide 278h corresponding to positions 458–474 of the human hsp65 molecule, 278m corresponding to positions 458–474 of the murine hsp65, and 278cox corresponding to positions 437–453 of the Coxiella burnetti hsp65 protein, said control peptides having the sequences depicted below:
278h N E D Q K I G I E I I K R T L K I (SEQ ID NO:2)
278m N E D Q K I G I E I I K R A L K I (SEQ ID NO:3)
278cox N E D Q R V G V E I A R R A M A Y (SEQ ID NO:4)

A further control peptide, AcR259–271, corresponds to positions 259–271 of the murine acetylcholine receptor α-chain and has the sequence:
V I V E L I P S T S S A V This peptide is recognized by T cells in the context of MHC class II molecules of the H-2d haplotype.

c. Reversed-phase HPLC: The purity of the peptide products was estimated by using the analytical HPLC column RP18 (Merck, Darmstadt, Germany) employing the SP8750 liquid chromatography system equipped with a SP8733 variable wavelength detector in water-acetonitrile gradients containing 0.1% trifluoroacetic acid (TFA). The effluents were monitored by UV absorbance at 220 nm. Acetonitrile of HPLC grade was purchased from Merck (Darmstadt, Germany). Peptides were further analyzed by amino acid analysis.

d. Vi: The Vi purified from Citrobacter freundii WR7011 (kindly donated by J. B. Robbins and S. C. Szu, National Institute of Health, Bethesda, Md., U.S.A.) contained <1% (each) protein, nucleic acid, and lipopolysaccharide. The molecular size of the Vi was estimated to be $3 \times 10^3$ kD. The Vi-fragments of about 45 kD were prepared by ultrasonic irradiation and were kindly provided by Dominique Schulz (Pasteur-Merieux, France).

e. Coupling of Vi and Vi-fragments with peptide:
Procedure 1 (see scheme 1) Conjugation of Vi/Vi-fragments and peptide without a spacer. One part of Vi/Vi-fragment and one part of peptide were dissolved in a minimal volume of double distilled water (ddw) and incubated for 12 hours at room temperature (RT) at pH 6 in the presence of two parts water-soluble carbodiimide (CDI; 1-(3-dimethylaminopropyl)-3-ethylcarbodiimide hydrochloride). After dialysis of the reaction mixture, the peptide density in the conjugate was determined by amino acid analysis and the sugar content of the construct estimated by Fourier transformed infrared spectroscopy (FTIR).

Procedure 2 (see scheme 1) Coupling of Vi/Vi-fragments and peptide following extension of peptide chain by a spacer in solution. In order to activate the carboxyl-function of the tBoc-ε-aminocaproic acid (t-Boc-AC) by N-hydroxysuccinimide, 1 mmol t-Boc-AC was mixed with 1.15 mmol N-hydroxysuccinimide in a minimal volume of dioxane (Merck, Germany); 1.15 mmol N,N'-dicyclohexylcarbodiimide (DCC) dissolved in dioxane was added, and after 3 hours the reaction mixture was filtered and washed with dioxane. 0.1 mmol of the desired peptide was dissolved in a small amount of ddw and mixed with 0.2 mmol $KHCO_3$, (Merck). The solution, in dioxane, of the N-hydroxysuccinimide ester of t-BocAC and the prepared peptide solution were mixed and reacted for 1 hour with vigorous mixing. The reaction mixture was then diluted with ddw (10 ml), cooled and acidified with 1N $KHSO_4$, solution. The product was extracted by ethyl acetate. The organic solution was washed with ddw, dried over $Na_2SO_4$, and evaporated to dryness. After drying the product for 2 hours over $P_2O_5$, dissolving it with 4–5 ml TFA and reacting for 10 minutes, the liquid was evaporated in vacuum at 30° C. The compound was washed twice with $CH_2Cl_2$ and the fluid evaporated before drying 2–3 hours over $P_2O_5$. Subsequently, the peptide-AC product was dissolved in ddw and the pH adjusted to 8. Five mg N-hydroxysuccinimide ester (prepared as described in Procedure 2 of Patent Application No. 102687) of Vi/Vi-fragments were added. After several hours of incubation, the resulting Vi-AC-Peptide conjugate was dialysed against ddw. The peptide density in the conjugate was estimated by amino acid analysis.

f. Immunization: Female mice belonging to different strains, 2–3 months old, were immunized subcutaneously (sc), two times 4 weeks apart with Vi/Vi-fragment alone or the Vi/Vi-fragment-conjugate. The injected amount of antigen varied from experiment to experiment and is indicated in the figures. The used adjuvant was in all cases IFA. Mice from each experimental group were bled 12 days after each injection.

g. Serology: Vi/Vi-fragment antibody levels elicited in mice with native or conjugated Vi, were determined by an enzyme-linked immunosorbent assay (ELISA). Since negatively-charged polysaccharides do not attach well to the polystyrene commonly used in the solid-phase ELISA, positively charged methylated bovine serum albumin (BSA) was used to coat Vi/Vi-fragments on the solid surface with very little non-specific binding. In detail, 0.5 mg Vi were dissolved in 1 ml PBS and stirred for 1 hour at room temperature. Ten mg methylated BSA (Sigma) were suspended in 1 ml H$_2$O and the obtained solution filtered on a 0.8 μm filter. To prepare the coating solution, 1 ml of dissolved polysaccharide was stirred for 20 minutes at room temperature with 50 μl of the methylated BSA solution and subsequently diluted 1:20 in PBS. Nunclon delta Si microwell plates were coated for 3 hours at 37° C. with 100 μl coating solution per well (2.5 μg Vi/well). The plates wee washed five times with PBS containing 0.33% Brij35 (Sigma) and blocked with a solution of PBS and 1% dried skimmed milk for 2 hours at 37° C. After washing, 100 μl aliquots of diluted unknown sera and of diluted standard serum (dilution buffer containing 1% skimmed milk and 0.33% Brij35 in PBS) were added and the plates were incubated for 1 hour at 37° C. Reference and test sera were applied to the plates in duplicate. The non-bound antibodies were removed by washing and a 1:5000 dilution of goat anti-mouse IgG Fab$_2$-alkaline phosphatase conjugate (Sigma), in the case of the test sera, and rabbit anti-horse IgG Fab$_2$ enzyme conjugate, in the case of the standard serum, was added to the plates (100 μl/well). After an incubation of 2 hours at 37° C., the plates were washed and the bound antibody visualized by the addition of 100 μl substrate solution containing 0.6 mg/ml of p-nitrophenylphosphate (Sigma) in diethanolamine-H$_2$O pH 9.8. The enzyme reaction was stopped 20 minutes later by the addition of 10 μl 5N NaOH per well. Optical densities were read at 405 nm. The anti-Vi standard serum Burro 260, containing 550 mg Vi antibody/ml, was prepared by multiple intravenous injections of formalin-fixed Salmonella typhi Ty2 (kindly donated by J. B. Robbins and S. C. Szu, NIH, Maryland, U.S.A.). The results obtained are expressed as optical density read at 405 nm.

h. Lymph node Proliferation after peptide-immunization:

Groups of 3 mice of the designated mouse strain were immunized sc into the footpads with 20 μg peptide emulsified in 0.2 ml IFA/PBS (0.1 ml/foot). Draining lymph nodes were taken 10 days later. Lymph node cells (LNC) of immunized mice 5×10$^6$/well) were cultured in the presence of different antigens. Cultures were set up in 200 μl Eagles medium supplemented with 2 mM glutamine, nonessential amino acids, 1 mM sodium pyruvate, 100 U/ml penicillin, 100 mg/ml streptomycin, 5×10$^5$M β-mercaptoethanol (Fluka AG, Buchs, Switzerland) containing 1% of syngeneic normal mouse serum, in round bottom microtiter plates (Falcon). After four-five days incubation, $^3$H-thymidine (0.5 mCi of 5 Ci/mmol, Nuclear Research Center, Negev, Israel) was added. Sixteen hours later, cells were harvested and radioactivity was counted. Results are expressed as counts per minute (cpm) or as stimulation indices (SI). The SI was defined as the ratio of the mean cpm of test cultures (with antigen) and the mean cpm of control cultures (without antigen).

EXAMPLES

Example 1

Preparation of Vi-peptide conjugates

Conjugates of Vi/Vi-fragments with peptide 278e and the control peptides were prepared as described above.

The composition of the Vi-peptide conjugates is summarized in Table 1. The results presented in Table 1 indicate that the molar ratio of peptide per sugar monomer was variable. Peptide doses of 0.8–2.2 μg injected per mouse as sugar-peptide conjugate were shown to be most effective.

Example 2

Lymph node cell proliferation to peptide 278e in different mouse strains with varying major histocompatibility complex MHC) background.

2.1. Lymph node proliferation after immunization with free carrier peptide. In order to test if peptide 278e can be recognized by the immune system in the context of different alleles of the murine MHC, 2–3 month old female mice (three animals per group) were injected sc with 20 μg of free peptide 278e emulsified in IFA as described in Material & Methods herein and specific proliferation of lymph node cells to peptide 278e and control peptides.

As shown in FIG. 1, LNCs of BALB/c (H-2d) mice inoculated with peptide 278e showed clear specific proliferative responses to the latter whereas no proliferation occurred to control peptide 278m and 278cox. Thus, LNCs primed with peptide 278e do not cross-react with the homologous self-peptide 278m derived from the sequence of murine hsp65.

FIG. 2a–c demonstrates that peptide 278e was also recognized in the three different congenic B10 mouse strains. LNCs of B10.RIII mice (H-2$^r$) (FIG. 2a), B10.BR mice (H-2$^k$) (FIG. 2b) and B10.S mice (H-2$^s$) (FIG. 2c) showed significant higher proliferative responses to peptide 278e in the designated peptide concentrations than to the control peptide AcR259–271.

Figure 3:
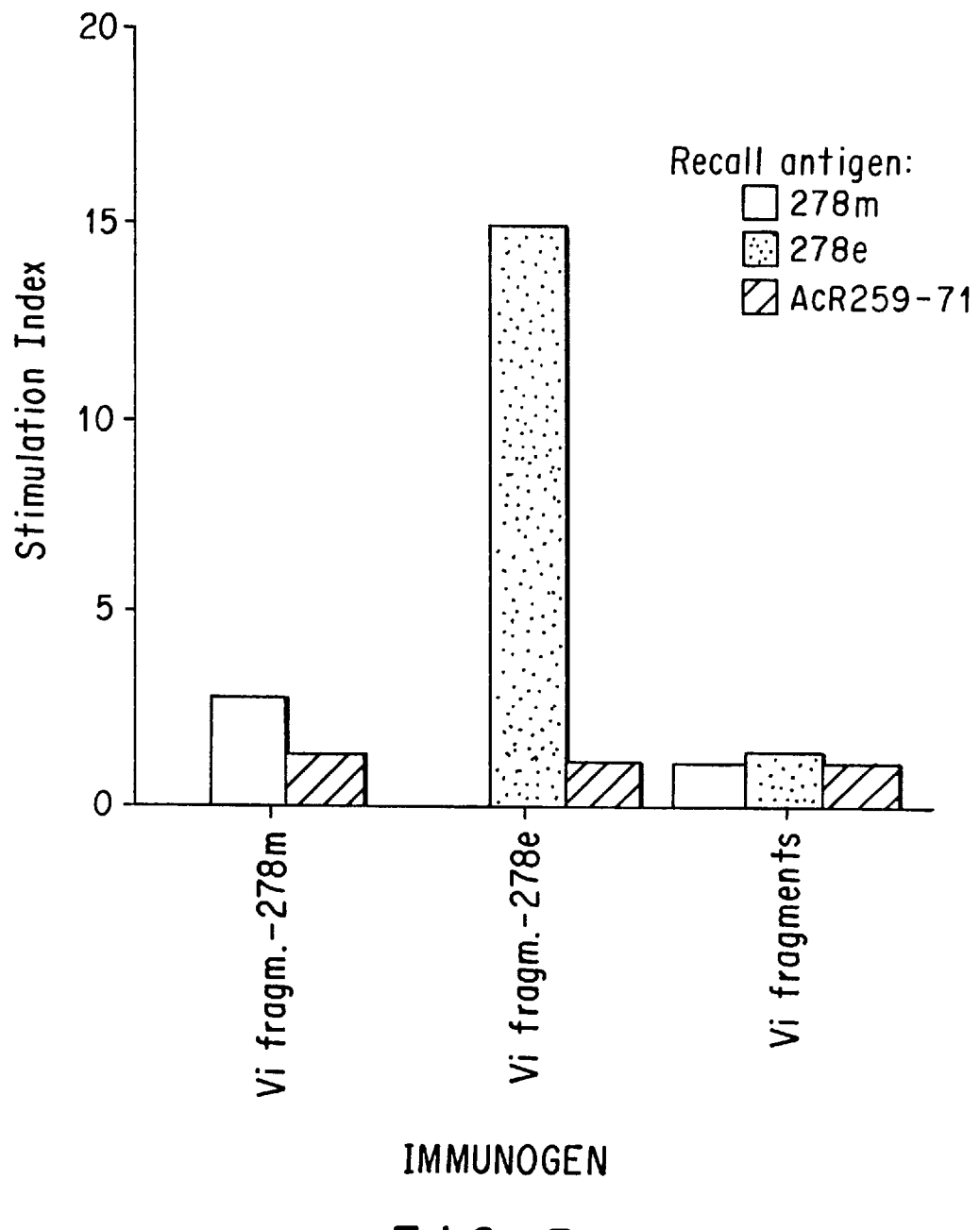
FIG. 3 illustrates lymph node proliferation to peptides 278e, 278m, and AcR259–271 after immunizing BALB/c mice with 2 µg Vi-fragments conjugated to 278 homologous or with 2 µg Vi-fragments alone.
Figure 4:
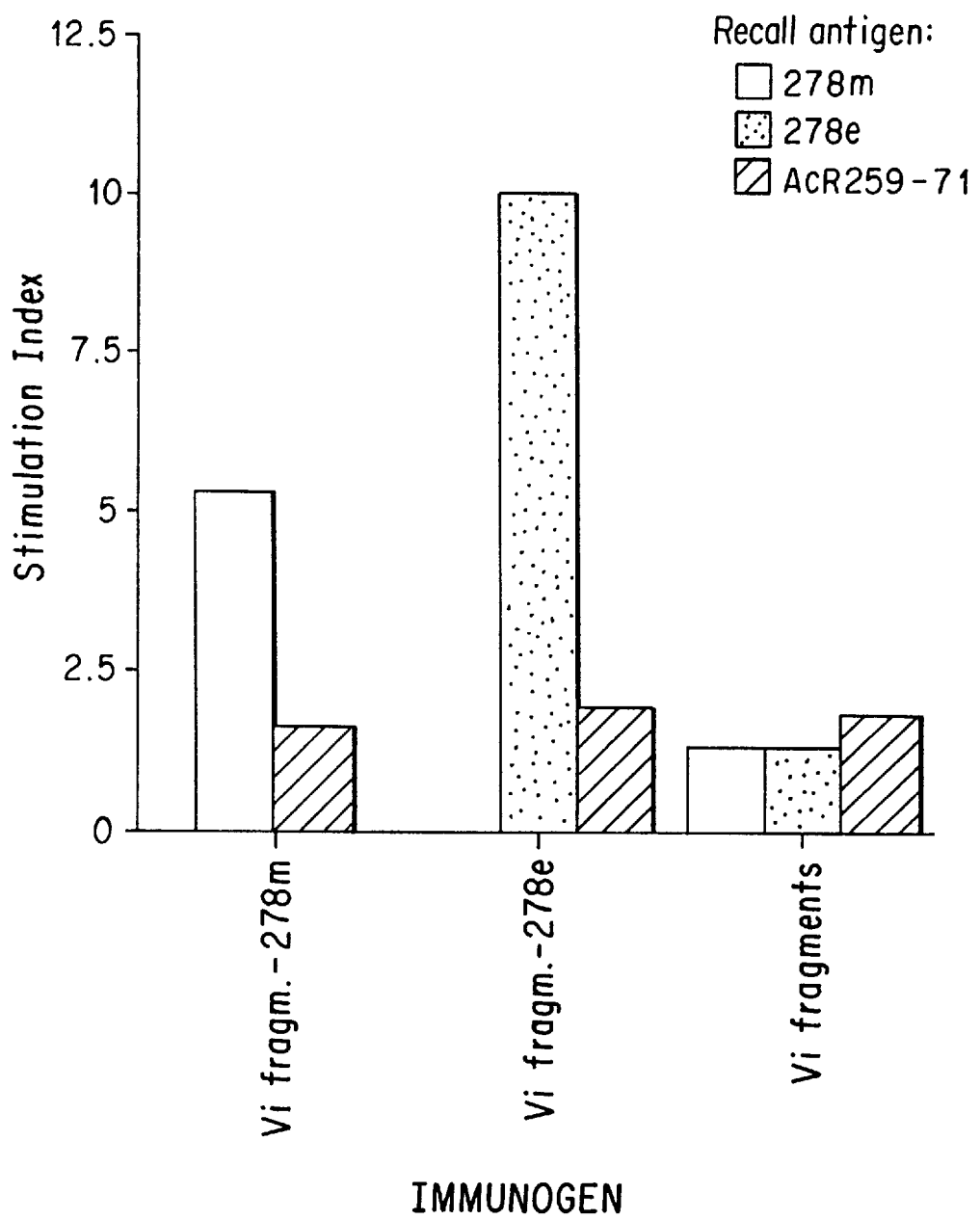
FIG. 4 illustrates lymph node proliferation to peptides 278e, 278m, and AcR259–271 after immunizing BALB/c mice with 20 µg Vi-fragments conjugated to 278 homologous or with 2 µgVi-fragments alone.

2.2. Lymph node cell proliferation to peptide 278e after immunization with peptide 278e conjugated to Vi-fragments. To analyze if coupling of peptide 278e to the polysaccharide Vi-fragments changes its antigenic structure, the LNC response to the peptide alone was tested after immunization with the sugar-peptide conjugate. FIG. 3 and FIG. 4 distinctly show that LNCs elicited by Vi-fragments-278e in BALB/c mice can recognize the unconjugated peptide when immunized with 2 μg Vi-fragments/mouse (FIG. 3) or 20 μg Vi-fragments/mouse (FIG. 4) as sugar-peptide conjugate (for the belonging injected peptide amount see Table 1).

TABLE 1

| Vi-fragment-peptide conjugate | Peptide amount injected per 2 μg Vi-fragment [μg] |
| --- | --- |
| Vi-fragments-278e | 0.8 |
| Vi-fragments-278m | 1.8 |
| Vi-fragments-278h | 2.2 |

Example 3

Figure 5:
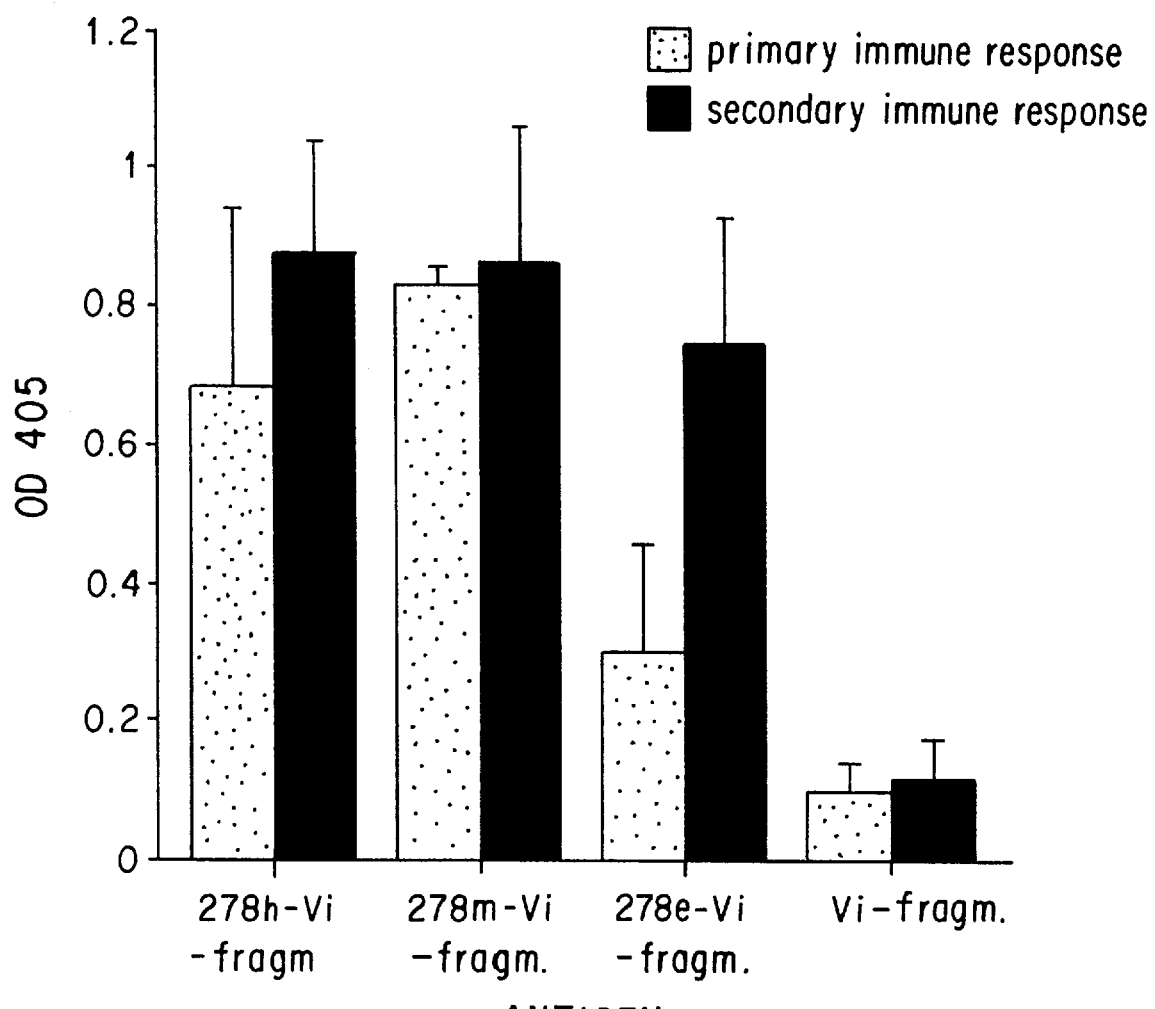
FIG. 5 shows the serum anti-Vi IgG antibody response induced in BALB/c mice by Vi-fragments alone or Vi-fragment-conjugates 278h-Vi, 278m-Vi, and 278e-Vi. The injected polysaccharide amount in each group was 2 µg. Primary and secondary immune responses are depicted. Results are shown at a serum dilution 1:100.

Antigenicity of Vi-fragments conjugated to peptide 278e. To examine if peptide 278e conjugated to Vi-fragments can enhance the immune response to this T-ind antigen, the immune response to the sugar was studied after inoculation of five BALB/c mice with the sugar-peptide conjugate. FIG. 5 clearly demonstrates that peptide 278e covalently linked to Vi-fragments can enhance the sugar-specific IgG antibody production substantially. Immunizing mice with a second dose of the conjugate gave rise to a strong booster effect indicating the involvement of T cells in the sugar-specific immune response. Inoculating BALB/c mice with the unconjugated polysaccharide only induced negligible levels of specific antibodies. The immune response induced by Vi-fragments-278e is compared to that elicited by the sugar conjugated to peptide 278h and 278m.

The above experiments offer evidence that peptide 278e can be recognized in association with a wide range of alleles of murine MHC molecules and can be used as carrier epitope for inducing enhanced immune responses to poorly immunogenic molecules. This evidence may be summarized a follows:

(i) Primed LNCs of mouse strains with varying genetic MHC-background were able to recognize peptide 278e by exhibiting specific proliferative responses.

(ii) Conjugating peptide 278e to Vi-fragments did not change its antigenic structure since LNCs primed with 278e coupled to the polysaccharide were still able to recognize the unbound peptide in an in vitro lymph node proliferation assay.

(iii) The immunogenicity of the Vi-fragments was increased when presented to the immune system as a conjugate coupled to peptide 278e.

The fact that LNCs that were primed with peptide 278e were not cross-reacting with the mouse homologue peptide 278m, indicates that peptide 278e used as carrier epitope probably will not induce immune responses directed to self components.

Since the immune response to peptide 278e seems not to be genetically restricted in mice, this synthetic peptide and analogs thereof might be used as universal carriers for the preparation of immunogenic conjugates to provide protective immunity against different pathogenic agents and can be suitable for the development of synthetic vaccines.

REFERENCES

—Avery, O. T. and Goebel, W. F., J. Exp- Med. 50:533–550 (1929)
—Babbitt, B. et al., Nature, 317:359–361 (1985)
—Barrios, C., et al., Eur. J. Immunol. 22:1365–1372 (1992)
—Brett, S., J., Cease, K., B., & Berzofsky, J. A., J. Exp. Med., 168:357–373 (1988)
—Herzenberg, L. A. & Tokuhisa T., J. Exp. Med., 155: 1730–1740 (1982)
—Kappler, J., Roehn N., & P. Marrack, Cell, 49, -(1987)
—Kent, S. B. H., Hood, L. E., Beilan, H., Maister, S., & T. Geiser, Peptides by U. Ragnarsson, Stockholm (1984)
—Lussow, A. R. et al., Immunol. Letters 25:255–263 (1990)
—Lussow, A. R. et al., Eur. J. Immunol. 21:2297–2302 (1991)
—Munk, M. E. et al., Eur. J. Immunol. 18:1835–1838 (1988)
—Perraut, R., Lussow, A. R., Gavoille, S., Garraud, O., Matile, H., Tougne, C., van Embden, J., van der Zee, R. Lambert, P.-H., Gysin, J., & G. Del Giudice, Clin. Exp. Immunol., 93:382–386 (1993)
—Stone, A. L., & Szu S. C., J. Clin. Microbio., 26:719–725 (1988)
—Young, D. et.al., Proc. Natl. Acad. Sci. USA 85:4267–4270 (1988)

We claim:

1. A conjugate comprising an antigen covalently attached to a synthetic peptide carrier constituting a T cell epitope of E. coli hsp65 in which said synthetic peptide carrier is selected from the group of peptides consisting of
   (a) NEDQNVGIKVALRAMEA (Pep278e) (SEQ ID NO:1), and
   (b) an analog of Pep278e (SEQ ID NO:1):

437                                           453
   N E D Q N V G I K V A L R A M E A, in which the residue $N^{437}$ is either N or Q, the residue $E^{438}$ is either E or D; the residue $D^{439}$ is either D or E; the residue $E^{452}$ is either E or D; the residue $Q^{440}$ is either Q or N, the residue $K^{445}$ is either K or R; the residue $V^{442}$ is I, L, V, M, F, norleucine (Nle) or norvaline (Nva): the residue $I^{444}$ residue is I, L, V, M, F, Nle or Nva; the residue $V^{446}$ is I, L, V, M, F, Nle or Nva; the residue $L^{448}$ is L, I, V, M, F, Nle or Nva; the residue $R^{449}$ is either R or K; and the residue $M^{451}$ is M, I, V, L, F, Nle or Nva,
said peptide or analog being capable of increasing substantially an antibody response to the antigen when the conjugate is administered in vivo.

2. The conjugate according to claim 1 wherein the antigen is a peptide, a protein or a polysaccharide.

3. The conjugate according to claim 2 wherein the peptide is derived from HIV virus or from malaria antigen.

4. The conjugate according to claim 2 wherein the polysaccharide is a bacterial polysaccharide.

5. A conjugate according to claim 1 wherein the synthetic peptide carrier is Pep278e (SEQ ID NO:1).

6. The conjugate according to claim 1 wherein the synthetic peptide carrier or analog is directly covalently attached to the antigen molecule.

7. The conjugate according to claim 6 wherein the antigen molecule is a bacterial polysaccharide.

8. The conjugate according to claim 7 wherein the bacterial polysaccharide is the capsular polysaccharide (CPS) Vi of Salmonella typhi.

9. The conjugate according to claim 1 wherein the synthetic peptide carrier or analog is covalently attached to the antigenic molecule through a spacer, selected from —O—R—CO—, —NH—R—CO—, —NH—R—NH—, —O—R—NH— or —NH—R—CH$_2$—, in which R is a saturated or unsaturated hydrocarbon chain optionally substituted and/or interrupted by one or more aromatic radicals or by heteroatoms selected from N, O or S.

10. The conjugate according to claim 9 wherein R is an aliphatic hydrocarbon chain containing 3–16 carbon atoms.

11. The conjugate according to claim 10 wherein R is the residue of ε-aminocaproic acid.

12. The conjugate according to claim 11 of the formula

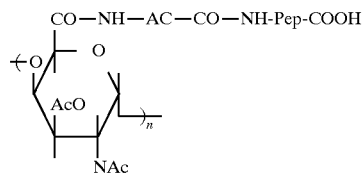

in which Ac is acetyl, AC is the residue of ε-aminocaproic acid, Pep is the residue of the peptide carrier Pep278e (SEQ ID NO:1) and the saccharide residue represents a repeating unit of the Vi capsular polysaccharide of Salmonella typhi.

13. The conjugate according to claim 12 which induces antibodies mainly of the IgG isotype.

14. A vaccine comprising a conjugate as claimed in claim 1, 6 or 9.

15. The vaccine according to claim 14 which contains an adjuvant.

16. A method for increasing an antibody response to an antigen molecule which comprises linking an antigen to a synthetic peptide carrier constituting a T cell epitope of E. coli hsp65 in which said synthetic peptide carrier is selected from the group of peptides consisting of
   (a) NEDQNVGIKVALRAMEA (Pep278e) (SEQ ID NO:1), and
   (b) an analog of Pep278e (SEQ ID NO:1):

437                                           453
   N E D Q N V G I K V A L R A M E A, in which the residue $N^{437}$ is either N or Q; the residue $E^{438}$ is either E or D; the residue $D^{439}$ is either D or E; the residue $E^{452}$ is either E or D; the residue $Q^{440}$ is either Q or N; the residue $K^{445}$ is either K or R; the residue $V^{442}$ is I, L, V, M, F, norleucine (Nle) or norvaline (Nva); the residue $I^{444}$ residue is I, L, V, M, F, Nle or Nva; the residue $V^{446}$ is I, L, V, M, F, Nle or Nva; the residue $L^{448}$ is L,
   I, V, M, F, Nle or Nva; the residue $R^{449}$ is either R or K;
   and the residue $M^{451}$ is M, I, V, L, F, Nle or Nva,
said peptide or analog being capable of increasing substantially an antibody response to the antigen when the conjugate is administered in vivo.

17. The method according to claim 16 in which the antigen molecule is a peptide, a protein or a polysaccharide.

18. The method according to claim 16 in which the antigen molecule is a bacterial polysaccharide.

19. A method for immunization of a mammalian host which comprises administering to said host an effective amount of a conjugate of claim 1, 6 or 9.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) NAME/KEY: Peptide
        ( B ) LOCATION: 1..17
        ( D ) OTHER INFORMATION: /label=Pep278e
            / note= "Corresponds to positions 437-453 of the E. coli hsp65 molecule."

( x i ) SEQUENCE DESCRIPTION: SEQ ID NO:1:

Asn Glu Asp Gln Asn Val Gly Ile Lys Val Ala Leu Arg Ala Met Glu
1               5                   10                  15

Ala ( 2 ) INFORMATION FOR SEQ ID NO:2:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) NAME/KEY: Peptide
        ( B ) LOCATION: 1..17
        ( D ) OTHER INFORMATION: /label=Pep278h
            / note= "Corresponds to positions 458-474 of the human hsp65 molecule."

(x i) SEQUENCE DESCRIPTION: SEQ ID NO:2:

Asn Glu Asp Gln Lys Ile Gly Ile Glu Ile Ile Lys Arg Thr Leu Lys
1               5                   10                  15

Ile (2) INFORMATION FOR SEQ ID NO:3:

(i) SEQUENCE CHARACTERISTICS:
      (A) LENGTH: 17 amino acids
      (B) TYPE: amino acid
      (C) STRANDEDNESS:
      (D) TOPOLOGY: unknown (i i) MOLECULE TYPE: peptide (i x) FEATURE:
      (A) NAME/KEY: Peptide
      (B) LOCATION: 1..17
      (D) OTHER INFORMATION: /label=Pep278m
          / note= "Corresponds to positions 458-474 of the murine
            hsp65 protein."

(x i) SEQUENCE DESCRIPTION: SEQ ID NO:3:

Asn Glu Asp Gln Lys Ile Gly Ile Glu Ile Ile Lys Arg Ala Leu Lys
1               5                   10                  15

Ile (2) INFORMATION FOR SEQ ID NO:4:

(i) SEQUENCE CHARACTERISTICS:
      (A) LENGTH: 17 amino acids
      (B) TYPE: amino acid
      (C) STRANDEDNESS:
      (D) TOPOLOGY: unknown (i i) MOLECULE TYPE: peptide (i x) FEATURE:
      (A) NAME/KEY: Peptide
      (B) LOCATION: 1..17
      (D) OTHER INFORMATION: /label=Pep278cox
          / note= "Corresponds to positions 437-453 of Coxiella
            burnetti hsp65 protein."

(x i) SEQUENCE DESCRIPTION: SEQ ID NO:4:

Glu Gly Asp Glu Ala Thr Gly Ala Asn Ile Val Lys Val Ala Leu Glu
1               5                   10                  15

Ala (2) INFORMATION FOR SEQ ID NO:5:

(i) SEQUENCE CHARACTERISTICS:
      (A) LENGTH: 13 amino acids
      (B) TYPE: amino acid
      (C) STRANDEDNESS:
      (D) TOPOLOGY: unknown (i i) MOLECULE TYPE: peptide (i x) FEATURE:
      (A) NAME/KEY: Peptide
      (B) LOCATION: 1..13
      (D) OTHER INFORMATION: /label=AcR259-271
          / note= "Corresponds to positions 259-271 of the murine
            acetyl-choline receptor '-chain."

(x i) SEQUENCE DESCRIPTION: SEQ ID NO:5:

Val Ile Val Glu Leu Ile Pro Ser Thr Ser Ser Ala Val
1               5                   10